United States Patent
Terada et al.

[11] Patent Number: 5,420,117
[45] Date of Patent: May 30, 1995

[54] 5-SUBSTITUTED URIDINE DERIVATIVES

[75] Inventors: Tadafumi Terada; Katsuhiko Fujimoto; Junichi Yamashita; Mitsugi Yasumoto, all of Honjo; Setsuo Takeda, Myozai; Junji Uchida, Tokushima; Konstanty Wierzba, Itano; Yuji Yamada, Tokushima, all of Japan

[73] Assignee: Taiho Pharmaceutical Co., Ltd., Tokyo, Japan

[21] Appl. No.: 963,250

[22] Filed: Oct. 19, 1992

Related U.S. Application Data

[63] Continuation of Ser. No. 465,211, Mar. 8, 1990, abandoned.

[30] Foreign Application Priority Data

Jul. 11, 1988 [JP] Japan ................ 63-173061
Sep. 19, 1988 [JP] Japan ................ 63-234282

[51] Int. Cl.⁶ .................. A61K 31/505; C07H 19/06
[52] U.S. Cl. ...................... 514/50; 536/28.55
[58] Field of Search ............ 536/23, 25.31, 25.32, 536/28.52; 514/49, 50

[56] References Cited

U.S. PATENT DOCUMENTS

| | | | |
|---|---|---|---|
| 4,334,059 | 6/1982 | Ogilvie | 536/28.52 |
| 4,472,386 | 9/1984 | Kodama et al. | 536/28.52 |
| 4,762,823 | 8/1988 | Watanabe et al. | 536/28.52 |
| 4,871,837 | 10/1989 | Magnusson et al. | 536/17.1 |
| 4,916,121 | 4/1990 | Saneyoshi et al. | 514/49 |
| 4,992,534 | 2/1991 | Fujii et al. | 514/49 |
| 5,198,540 | 3/1993 | Koster . | |

FOREIGN PATENT DOCUMENTS 51-52183 5/1976 Japan .
4151987 5/1978 Japan ................ 54/50
60-67492 4/1985 Japan .

*Primary Examiner*—Douglas W. Robinson
*Assistant Examiner*—J. Oliver Wilson
*Attorney, Agent, or Firm*—Nikaido, Marmelstein, Murray & Oram

[57] ABSTRACT

This invention provides a 5-substituted uridine derivative of the formula

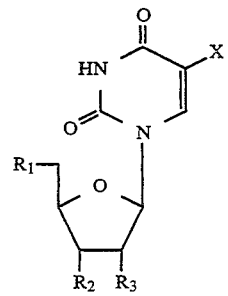

wherein X is F or $CF_3$, $R_1$ and $R_2$ each represent a group $-OSi-(R_4)(R_5)(R_6)$ (wherein $R_4$, $R_5$ and $R_6$ represent $C_1-C_{10}$ alkyl or the like), OH, aminoacyloxy group wherein the amino group may be substituted with lower alkyl group or carboxylalkylcarbonyloxy group, $R_3$ is a group $-OSi(R_4)(R_5)(R_6)$, H, OH, aminoacyloxy group wherein the amino group may be substituted with lower alkyl group, or carboxylalkylcarbonyloxy group, and at least one of $R_1$, $R_2$ and $R_3$ is a group $-OSi-(R_4)(R_5)(R_6)$, with the proviso that when X is fluorine atom, $R_3$ is not hydrogen, and an intermediate for the preparation thereof, preparation processes of the derivative and anti-tumor agent containing the derivative as an active ingredient.

6 Claims, No Drawings

5-SUBSTITUTED URIDINE DERIVATIVES

This application is a continuation of application Ser. No. 465,211, filed Mar. 8, 1990, now abandoned.

BACKGROUND OF THE INVENTION

1. Field of the Invention

The present invention relates to 5-substituted uridine derivatives which are novel substances and 5'-trityl-5-substituted uridine derivatives which are useful as intermediates for preparing the 5-substituted uridine derivatives. The 5-substituted uridine derivatives of this invention are useful for treating tumors.

2. Description of the Related Art

5-Fluorouridine (hereinafter referred to as "FUR"), which was synthesized in 1959, is known for its excellent activity against malignant tumors (U.S. Pat. No. 2885398). However, FUR has a problem on clinical use because of its high toxicity.

Many attempts have been made to resolve this problem by converting FUR into various derivatives (Japanese Unexamined Patent Publications Nos.64280/1975; 52183/1976; 91997/1982; 246196/1986). However, such attempts failed to give useful derivatives.

5-Trifluoromethyl-2'-deoxyuridine (hereinafter referred to as "F$_3$TdR") represented by the formula

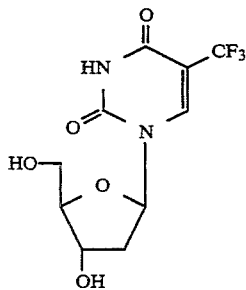

has an anti-tumor activity [Cancer Research 24, 1979 (1964)] and a strong antiviral activity [Cancer Research 30, 1549, 1970]. In view of these activities, various investigations have been made on the utility of F$_3$TdR as pharmaceuticals, but without developing a useful compound.

SUMMARY OF THE INVENTION

In the foregoing situation, we conducted extensive research to develop 5-substituted uridine derivatives which are lower in toxicity and more useful for treating tumors than said FUR and F$_3$TdR, and found that the 5-substituted uridine derivatives of this invention can achieve this object and that 5'-trityl-5-substituted uridine derivatives are useful as intermediates for preparing 5-substituted uridine derivatives. This invention has been accomplished based on these novel findings.

According to the present invention, there are provided:

(1) a 5-substituted uridine derivative represented by the formula

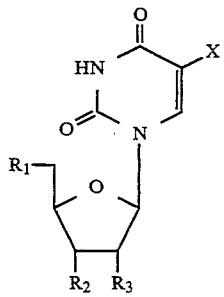

wherein X is fluorine atom or trifluoromethyl group, R$_1$ and R$_2$ each represent (a) a group represented by the formula —OSi—(R$_4$)(R$_5$)(R$_6$) (wherein R$_4$, R$_5$ and R$_6$ are the same or different and each represent alkyl group having 1 to 10 carbon atoms, a group represented by the formula —(CH$_2$)$_n$Ph (wherein n is 0 to 2 and Ph is phenyl group) or a group represented by the formula —OSi—(R$_7$)(R$^8$)(OH) (wherein R$_7$ and R$_8$ are the same or different and each represent lower alkyl group)), (b) hydroxyl group, (c) aminoacyloxy group in which the amino group may optionally be substituted with lower alkyl group or (d) carboxylalkylcarbonyloxy group, R$_3$ is a group represented by the formula —OSi—(R$_4$)(R$_5$)(R$_6$) (wherein R$_4$, R$_5$ and R$_6$ are as defined above), hydrogen atom, hydroxyl group, aminoacyloxy group in which the amino group may optionally be substituted with lower alkyl group, or carboxylalkylcarbonyloxy group, provided that at least one of R$_1$, R$_2$ and R$_3$ is a group represented by the formula —OSi—(R$_4$)(R$_5$)(R$_6$) (wherein R$_4$, R$_5$ and R$_6$ are as defined above) and that when X is fluorine atom, R$_3$ is not hydrogen, or a pharmaceutically acceptable salt thereof, and (2) a 5-substituted-5'-trityluridine derivative represented by the formula

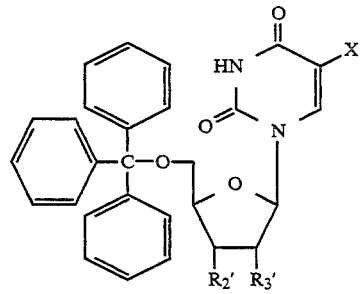

wherein X is fluorine atom or trifluoromethyl group, R$_2$' is hydroxyl group or a group represented by the formula —OSi—(R$_4$)(R$_5$)(R$_6$) (wherein R$_4$, R$_5$ and R$_6$ are the same or different and each represent alkyl group having 1 to 10 carbon atoms, a group represented by the formula —(CH$_2$)$_n$Ph (wherein n is 0 to 2 and Ph is phenyl group) or a group represented by the formula —OSi—(R$_7$)(R$_8$)(OH) (wherein R$_7$ and R$_8$ are the same or different and each represent lower alkyl group)), R$_3$' is hydrogen atom, hydroxyl group or a group represented by the formula —OSi—(R$_4$)(R$_5$)(R$_6$) (wherein R$_4$, R$_5$ and R$_6$ are as defined above), provided that at least one of R$_2$ and R$_3$' is a group represented by the formula —OSi—(R$_4$)(R$_5$)(R$_6$) (wherein R$_4$, R$_5$ and R$_6$ are as defined above) and that when X is fluorine atom, R$_3$' is not hydrogen atom.

According to the present invention, there is further provided an agent for heating tumors containing as an effective component the compound of the formula (I) or a pharmaceutically acceptable salt thereof.

According to the present invention, there is further provided a method for treating tumors, characterized by administering to a mammal an effective amount of the compound of the formula (I) or a pharmaceutically acceptable salt thereof.

The 5-substituted uridine derivatives of the formula (I) according to this invention have a lower toxicity and are more useful for treating tumors than FUR and $F_3TdR$, hence useful as medicaments. The 5'-trityl-5-substituted uridine derivatives of the formula (II) are useful as intermediates for preparing the compounds of the formula (I).

Examples of aminoacyloxy groups with the amino group optionally substituted with lower alkyl group which are represented by $R_1$, $R_2$ and $R_3$ in the formula (I) are acyloxy groups, particularly alkylcarbonyloxy groups, having 2 to 6 carbon atoms, which is substituted with one or two amino groups wherein one or two hydrogen atoms attached to the nitrogen atom may optionally be substituted with lower alkyl group, particularly alkyl group having 1 to 4 carbon atoms, such as methyl, ethyl, propyl or the like. Examples of such aminoacyloxy groups are glycyloxy, N,N-dimethylglycyloxy, alanyloxy, α-aminoisobutyryloxy, α-aminobutyryloxy, α-N,N-dimethylaminobutyryloxy, N,N-diethylalanyloxy, valyloxy, leucyloxy, isoleucyloxy, ornithinyloxy, lysinyloxy, α,β-di(dimethylamino)propionyloxy, etc. Examples of carboxylalkylcarbonyloxy groups are those having 3 to 6 carbon atoms such as carboxylmethylcarbonyloxy, 2-carboxylethylcarbonyloxy, 2-carboxylpropylcarbonyloxy, 3-carboxylpropylcarbonyloxy, 4-carboxylbutylcarbonyloxy, etc.

Examples of alkyl groups having 1 to 10 carbon atoms represented by $R_4$, $R_5$ and $R_6$ are straight- or branched-chain alkyl groups such as methyl, ethyl, propyl, isopropyl, butyl, sec-butyl, tert-butyl, pentyl, neopentyl, hexyl, 2,3-dimethyl-2-butyl, heptyl, octyl, nonyl, decyl, etc. Examples of lower alkyl groups represented by $R_7$ and $R_8$ are straight- or branched-chain alkyl groups having 1 to 6 carbon atoms such as methyl, ethyl, propyl, isopropyl, butyl, sec-butyl, tert-butyl, pentyl, neopentyl, hexyl, etc.

Of the compounds of the formula (I), preferred compounds are those wherein X is fluorine atom, one or two of $R_1$, $R_2$ and $R_3$ represent(s) a group of the formula $-OSi-(R_4')(R_5')(R_6')$ (wherein $R_4'$, $R_5'$ and $R_6'$ are the same or different and each represent alkyl group having 1 to 8 carbon atoms, benzyl group, 2-phenylethyl group or a group represented by the formula $-OSi-(R_7)(R_8)(OH)$ (wherein $R_7$ and $R_8$ are the same or different and each represent lower alkyl)), the remaining one or two of $R_1$, $R_2$ and $R_3$ represent(s) hydroxyl group, aminoalkylcarbonyloxy group with the amino group optionally substituted with lower alkyl group, or carboxylalkylcarbonyloxy group. Of these preferred compounds, more preferred are the compounds wherein $R_1$ is the group represented by the formula $-OSi-(R_4')(R_5')(R_6')$ (wherein $R_4'$, $R_5'$ and $R_6'$ are as defined above), $R_2$ and $R_3$ are the same and each represent hydroxyl group, aminoalkylcarbonyloxy group with the amino group optionally substituted with lower alkyl group, or carboxylalkylcarbonyloxy group, and the compounds wherein $R_1$ is hydroxyl group, $R_2$ and $R_3$ are the same and each represent the group represented by the formula $-OSi-(R_4')(R_5')(R_6')$ (wherein $R_4'$, $R_5'$ and $R_6'$ are as defined above).

Also preferable are the compounds of the formula (I) according to the invention wherein X is trifluoromethyl group, $R_3$ is hydrogen atom, one of $R_1$ and $R_2$ is a group represented by the formula $-OSi-(R_4')(R_5')(R_6')$ (wherein $R_4'$, $R_5'$ and $R_6'$ are the same or different and each represent alkyl group having 1 to 8 carbon atoms, benzyl group, 2-phenylethyl group or a group represented by the formula $-OSi-(R_7)(RS)(OH)$ (wherein $R_7$ and $R_8$ are the same or different and each represent lower alkyl group)), the other of $R_1$ and $R_2$ is hydroxyl group, aminoalkylcarbonyloxy group with the amino group optionally substituted with lower alkyl group, or carboxyalkylcarbonyloxy group, or both of $R_1$ and $R_2$ are the group represented by the formula $-OSi-(R_4')(R_5')(R_6')$ (wherein $R_4'$, $R_5'$ and $R_6'$ are as defined above).

More preferred compounds of the formula (I) are those described in items (i) and (ii) below:

(i) compounds of the formula (I) wherein X is fluorine atom, one or two of $R_1$, $R_2$ and $R_3$ represent(s) tertbutyldimethylsilyloxy group, dimethyloctylsilyloxy group or benzyldimethylsilyloxy group, the remaining one or two of $R_1$, $R_2$ and $R_3$ represent(s) hydroxyl group, glycyloxy group with the amino group optionally substituted with lower alkyl group, or carboxyethylcarbonyloxy group and (ii) compounds of the formula (I) wherein X is trifluoromethyl group, $R_3$ is hydrogen atom, one of $R_1$ and $R_2$ is tert-butyldimethylsilyloxy group or benzyldimethylsilyloxy group, the other of $R_1$ and $R_2$ is hydroxyl group, glycyloxy group with the amino group optionally substituted with lower alkyl group, or carboxylethylcarbonyloxy, or both of $R_1$ and $R_2$ are tertbutyldimethylsilyloxy group or benzyldimethylsilyloxy group.

As the more preferred compounds of the type (i), there may be mentioned the compounds of the formula (I) wherein X is fluorine atom, $R_1$ is tert-butyldimethylsilyloxy group, dimethyloctylsilyloxy group or benzyldimethylsilyloxy group, $R_2$ and $R_3$ are the same and each represent hydroxyl group, glycyloxy group with the amino group optionally substituted with lower alkyl group, or carboxyethylcarbonyloxy group; and compounds of the formula (I) wherein $R_1$ is hydroxyl group, and $R_2$ and $R_3$ are the same and each represent tert-butyldimethylsilyloxy group, dimethyloctylsilyloxy group or benzyldimethylsilyloxy group.

Especially preferred examples of compounds of the formula (I) are as follows:

5'-O-tert-butyldimethylsilyl-5-fluorouridine,
2', 3'-bis(O-tert-butyldimethylsilyl)-5-fluorouridine,
5'-O-dimethyloctylsilyl-5-fluorouridine,
5'-O-benzyldimethylsilyl-5-fluorouridine,
5'-O-tert-butyldimethylsilyl-2'3'-bis(O-dimethylglycyl)-5-fluorouridine,
5'-O-tert-butyldimethylsilyl-2'-deoxy-5-trifluoromethyluridine,
5'-O-tert-butyldimethylsilyl-2', 3'-bis(O-2-carboxyethylcarbonyl)-5-fluorouridine.

Preferred examples of compounds of the formula (II) which are the intermediates of the invention are as follows:

2'-O-tert-butyldimethylsilyl-5'-O-triphenylmethyl-5-fluorouridine,

3'-O-tert-butyldimethylsilyl-5'-O-triphenylmethyl-5-fluorouridine,

2',3'-bis(O-tert-butyldimethylsilyl)-5'-O-triphenylmethyl-5-fluorouridine,

2'-O-benzyldimethylsilyl-5'-O-triphenylmethyl-5-fluorouridine,

3'-O-tert-butyldimethylsilyl-5'-O-triphenylmethyl-2'-deoxy-5-trifluoromethyluridine.

Described below are processes for preparing the compounds of the formula (I) according to invention. The compound of the formula (I) can be prepared by any of the following processes A, B and C.

Process A

The compound of the formula (I) according to the invention can be prepared, as shown in a reaction scheme below, by reacting the compound of the formula (III) with the halogenosilyl compound of the formula (IV) in a solvent in the presence of a basic catalyst.

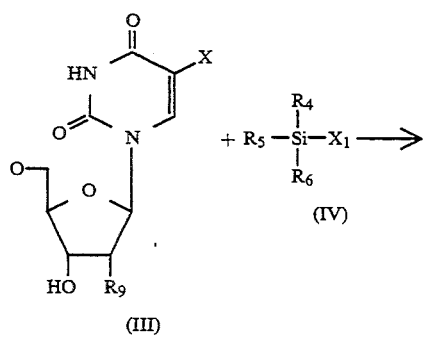

(III)

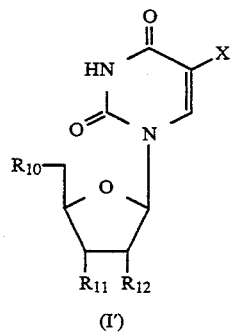

(I')

In the formulae, X, $R_4$, $R_5$ and $R_6$ are as defined above, $X_1$ is halogen atom, $R_9$ is hydrogen atom or hydroxyl group, $R_{10}$ and $R_{11}$ are hydroxyl group or a group represented by the formula —OSi—$(R_4)(R_5)(R_6)$ (wherein $R_4$, $R_5$ and $R_6$ are as defined above), $R_{12}$ is hydrogen atom, hydroxyl group or a group represented by the formula —OSi$(R_4)(R_5)(R_6)$ (wherein $R_4$, $R_5$ and $R_6$ are as defined above), and at least one of $R_{10}$, $R_{11}$ and $R_{12}$ is a group represented by the formula —OSi—$(R_4)(R_5)(R_6)$ (wherein $R_4$, $R_5$ and $R_6$ are as defined above), with the proviso that when X is fluorine atom, $R_9$ and $R_{12}$ are not hydrogen atom. Specific examples of halogen atoms represented by $X_1$ are chlorine, bromine and iodine atoms.

Insofar as the solvent used does not adversely affect the reaction, the solvent is not specifically limited. A wide range of conventional solvents can be used without specific limitation. Examples of useful solvents are benzene, toluene, xylene and like aromatic hydrocarbons, ether, tetrahydrofuran, dioxane and like ethers, acetonitrile, pyridine, dimethylformamide, dimethyl sulfoxide and like aprotic solvents, etc. These solvents are usable singly or at least two of them can be used in mixture.

Suitable examples of the basic catalyst are pyridine, dimethylaminopyridine, 2,6-lutidine, imidazole, triethylamine and like organic bases, etc.

The amount of the basic catalyst to be used is about 1 to about 10 moles, preferably about 1.5 to about 4 moles, per mole of the compound of the formula (III). The amount of the halogenosilyl compound of the formula (IV) to be used is about 0.5 to about 10 moles, preferably about 0.8 to about 3.1 moles, per mole of the compound of the formula (III).

The reaction temperature is 0° to about 80° C., preferably room temperature to about 50° C. The reaction time is variable depending on the kinds of the solvent and the basic catalyst to be used, but is usually about 0.5 to about 20 hours.

Process B

A 5'-trityl-5-substituted uridine derivative of the following formula (II')

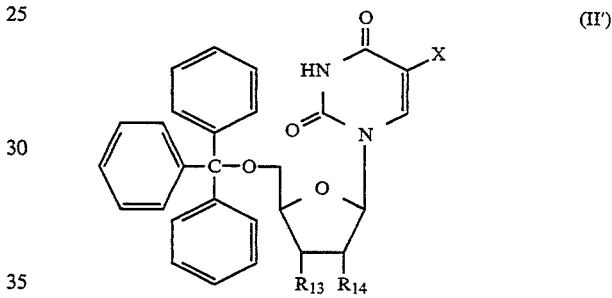

wherein X is fluorine atom or trifluoromethyl group, $R_{13}$ is hydroxyl group or a group represented by the formula —OSi—$(R_4)(R_5)(R_6)$, $R_{14}$ is hydrogen atom, hydroxyl group or a group represented by the formula —OSi—$(R_4)(R_5)(R_6)$, and at least one of $R_{13}$ and $R_{14}$ is a group represented by the formula —OSi—$(R_4)(R_5)(R_6)$, with the proviso that when X is fluorine atom, $R_{14}$ is not hydrogen atom; and $R_4$, $R_5$ and $R_6$ herein are as defined above, is subjected to reaction for removal of trityl in the presence of an acid catalyst, giving a compound of the invention represented by the formula (I'') given below:

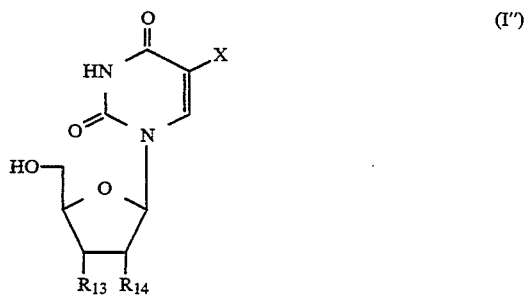

wherein X, $R_{13}$ and $R_{14}$ are as defined above.

Solvents usable in this reaction include the same solvents exemplified above with respect to process A. Examples of suitable acid catalysts are formic acid, acetic acid and like organic carboxylic acid, toluene-sulfonic acid and like organic sulfonic acids, etc.

The amount of the acid catalyst to be used is about 0.01 to about 10 moles, preferably about 0.05 to about 10 moles, per mole of the 5'-trityl-5-substituted uridine derivative of the formula (II').

The reaction temperature is 0° to about 130° C., preferably room temperature to about 80° C. The reaction time is about 0.5 to about 10 hours although variable depending on the kinds of the solvent and the basic catalyst to be used.

The intermediate of the invention, i.e., 5'-trityl-5-substituted uridine derivative of the formula (II') can be prepared, as illustrated in a reaction scheme below, by reacting a 5'-trityl-5-substituted uridine derivative of the formula (V) which is a known compound with the halogenosilyl compound of the formula (IV) in the presence of a basic catalyst.

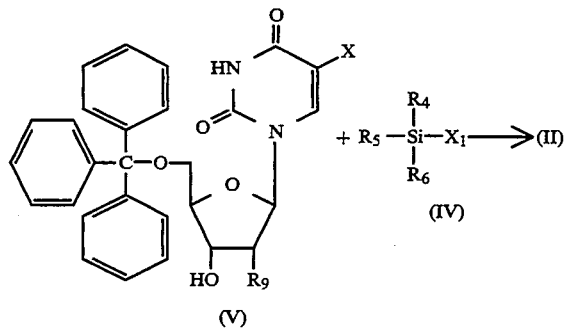

In the formulae, $R_9$, X and $X_1$ are as defined above.

The reaction conditions such as solvent, basic catalyst, reaction temperature, reaction time, the amounts of reactants, etc. are the same as specified in respect of process A.

Process C

The compound of the invention represented by the formula

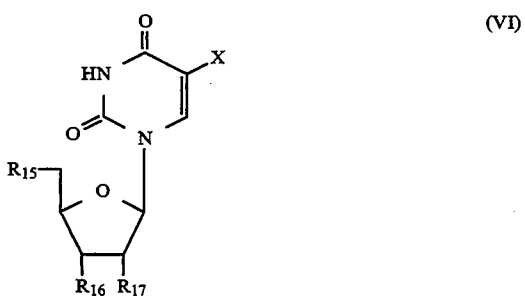

wherein X is as defined above, $R_{15}$ and $R_{16}$ represent a group of the formula $-OSi-(R_4)(R_5)(R_6)$, aminoacyloxy group with the amino group optionally substituted with lower alkyl or carboxylalkylcarbonyloxy group, $R_{17}$ is a group represented by the formula $-OSi-(R_4)(R_5)(R_6)$, aminoacyloxy group with the amino group optionally substituted with lower alkyl group, carboxylalkylcarbonyloxy group or hydrogen atom, at least one of $R_{15}$, $R_{16}$ and $R_{17}$ is a group represented by the formula $-OSi-(R_4)(R_5)(R_6)$ and at least one of $R_{15}$, $R_{16}$ and $R_{17}$ is aminoacyloxy group with the amino group optionally substituted with lower alkyl group, or carboxylalkylcarbonyloxy group, with the proviso that when X is fluorine atom, $R_{17}$ is not hydrogen atom; and $R_4$, $R_5$ and $R_6$ herein have the same meanings as above, can be prepared by reacting the compound obtained by process A or B and represented by the formula

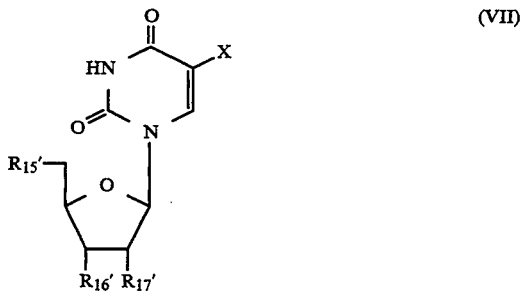

wherein X is as defined above, $R_{15}'$ and $R_{16}'$ represent hydroxyl group or a group represented by the formula $-OSi-(R_4)(R_5)(R_6)$, $R_{17}'$ is hydrogen atom, hydroxyl group or a group represented by the formula $-OSi-(R_4)(R_5)(R_6)$, at least one of $R_{15}'$, $R_{16}'$ and $R_{17}'$ is a group represented by the formula $-OSi-(R_4)(R_5)(R_6)$, and at least one of $R_{15}'$, $R_{16}'$ and $R_{17}'$ is hydroxyl group, with the proviso that when X is fluorine atom $R_{17}'$ is not hydrogen atom; and $R_4$, $R_5$ and $R_6$ herein are as defined above, with the carboxylic acid of the following formula (VIII) or a reactive derivative thereof, or an anhydride of the dicarboxylic acid of the following formula (IX) in the presence of a basic catalyst using or without using a condensation agent. The compound of the formula (VIII) or the formula (IX) or their reactive derivative is caused to react with the hydroxyl group represented by at least one of $R_{15}'$, $R_{16}'$ and $R_{17}'$ in the compound of the formula (VII).

$$R_{18}COOH \qquad (VIII)$$

In the formula, $R_{18}$ is aminoalkyl group, particularly $C_1$-$C_5$ aminoalkyl group, wherein the amino group may optionally be substituted with lower alkyl group.

$$HOOC-R_{19}-COOH \qquad (IX)$$

In the formula, $R_{19}$ is alkylene group, particularly $C_1$-$C_4$ alkylene group.

Examples of the reactive derivative of carboxylic acid of the formula (VIII) are acid halide, acid anhydride, etc. The use of a condensation agent which is not critical in the invention, enables smooth progress of reaction. Examples of useful condensation agent are N,N-dicyclohexylcarboxylimide, 2-chloro-1-methylpyridinium tosylate, etc. The amount of the condensation agent to be used is about 2 to about 6 moles, preferably about 2 to about 4 moles, per mole of the compound of the formula (VII).

Solvents useful in this reaction include, for example, methylene chloride, 1,2-dichloroethane, chloroform and like halogenated hydrocarbons, ether, tetrahydrofuran, dioxane and like ethers, etc. These solvents are usable singly or at least two of them can be used in mixture. Examples of suitable basic catalysts are pyridine, dimethylaminopyridine, 2,6-lutidine, imidazole, triethylamine and like organic bases, etc. The amount of the basic catalyst to be used is about 0.1 to about 20 moles, preferably about 5 to about 10 moles, per mole of the compound of the formula (VII).

A suitable amount of the compound of the formula (VIII) or the compound (IX) to be used is about 1 to 6 moles, preferably about 2 to about 4 moles, per mole of the compound of the formula (VII). The reaction temperature is 0° to about 60° C., preferably 0° to about 30° C. Although the reaction time is variable depending on the kinds of the solvent and basic catalyst to be used, the reaction is completed usually in about 0.1 to about 48 hours.

The 5-substituted uridine derivative of the invention thus obtained can be easily separated and purified by conventional separation and purification means such as recrystallization, reprecipitation, column chromatography or the like.

While usable per se as a drug for treating a malignant tumor, the compound of the invention can be made into a pharmaceutically acceptable salt to facilitate its dissolution in water and its absorption in the body. The pharmaceutically acceptable salt contains an acid component capable of forming a salt in combination with the aminoacyloxy group wherein the amino group may optionally be substituted with lower alkyl group of the compound of the formula (I) according to the invention or an alkali component capable of forming a salt in combination with the carboxylalkylcarbonyloxy group of the compound of the formula (I), and is not particularly limited insofar as the salt thus formed can exhibit the desired efficacy and is nontoxic or of low toxicity in the living body. Examples of the acid component are hydrogen chloride, hydrogen bromide, sulfuric acid, nitric acid, phosphoric acid and like inorganic acids, and p-toluenesulfonic acid, benzenesulfonic acid, formic acid, oxalic acid, succinic acid, malic acid, citric acid, tartaric acid and like organic acids. Examples of the alkali component are sodium, potassium and like alkali metals, calcium, magnesium and like alkaline earth metals, ammonia, methylamine, dimethylamine, piperidine, cyclohexylamine, triethylamine and like primary, secondary and tertiary amines, etc.

The salt can be prepared by a conventional process for producing a salt, for example by reacting the compound of the formula (I) with theoretical amount of the acid or alkali component in a suitable solvent.

When the salt is soluble in a solvent, the desired salt is produced by addition of a solvent incapable of dissolving the salt or by lyophilization. When the salt is fully insoluble in a solvent, the desired salt is obtained by filtering the formed salt. The salt obtained in this way can be purified with use of MCI gel (product of Mitsubishi Chemical Industries Limited, Japan) or the like.

The compound of the invention, when used as an agent for treating malignant tumors of mammals including humans, may take pharmaceutical dosage forms including parenteral preparations such as injections, suppositories, eye drops, aerosols and the like and oral preparations such as tablets, coated tablets, powders, granules, capsules, liquids and the like. Oral preparations are generally preferred. The above preparations are formulated in a manner known in the art. For the formulation of solid preparations for oral administration, an excipient, and if desired, a binder, disintegrator, lubricant, coloring agent, corrigent, flavor, etc. are added to the compound of the invention, and then tablets, coated tablets, granules, powders, capsules or the like are prepared in a conventional manner. For the formulation of injections, a pH adjusting agent, buffer, stabilizer, isotonic agent, local anesthetic or the like is added to the active ingredient of the invention, and injections for subcutaneous, intramuscular or intravenous administration can be prepared in a conventional manner. For the formulation of suppositories, a base, and if desired, a surfactant are added to the active ingredient of the invention, and the suppositories are prepared in a conventional manner. The excipients useful for the solid preparations for oral administration are those generally used in the art, and useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, schellac, sucrose, water, ethanol, propanol, carboxymethylcellulose, potassium phosphate and the like, lubricants such as magnesium stearate, talc and the like, and further include additives such as usual known coloring agents, disintegrators and the like. Examples of bases useful for the formulation of suppositories are, for example, oleaginous bases such as cacao butter, polyethylene glycol, lanolin, fatty acid triglycerides, Witepsol (trademark, Dynamite Nobel Co., Ltd.) and the like. Liquid preparations may be in the form of aqueous or oleaginous suspension, solution, syrup, elixir and the like, which can be prepared by a conventional way using usual additives.

The amount of the compound (I) of the invention to be incorporated into the pharmaceutical composition of the invention varies with the dosage form, solubility and chemical properties of the compound, administration route, administration scheme and the like. Preferably the amount is about 10 to about 15 w/w% in the case of oral preparations, and about 0.1 to about 1 w/w% in the case of injections which are parenteral preparations.

The dosage of the compound (I) of the invention is suitably determined depending on the individual cases taking symptoms, age and sex of the subject and the like into consideration. Usually, the dosage in the case of oral administration is about 100 to about 800 mg per day for an adult in 2 to 4 divided doses, and the dosage in the case of injection, for example, by intravenous administration is 2 ml (about 1 to about 10 mg) which is administered once a day for an adult wherein the injection may be diluted with physiological saline or glucose injection liquid if so desired, and slowly administered over at least 5 minutes. The dosage in the case of suppositories is about 1 to about 300 mg which is administered once or twice a day at an interval of 6 to 12 hours wherein the suppositories are administered by insertion into the rectum.

Given below are Preparation Examples. In the Preparation Examples that follow, the compound numbers correspond to the compound numbers used in the Examples to be described later.

Preparation Example 1: Tablets

| | |
|---|---|
| Compound 1 | 50 g |
| Lactose | 200 g |
| Corn starch | 80 g |
| Hydrolyzed starch | 20 g |
| Potassium stearate | 10 g |
| | 360 g |

Compound 1, lactose, corn starch and hydrolyzed starch were mixed, and granulated by adding water to prepare an active paste. After drying overnight at 45° C., the granules were sieved. Potassium stearate was added thereto and the tablets weighing 360 mg and having a diameter of 10 mm were produced by means of tabletting machine.

Preparation Example 2: Capsules

| Compound 4 | 25.0 g |
|---|---|
| Lactose | 150.0 g |
| Corn starch | 40.0 g |
| Talc | 5.0 g |
| Per capsule | 200 mg |

Compound 4, lactose and corn starch were mixed and pulverized. After addition of talc, the mixture was placed into hard gelatin capsules.

Preparation Example 3: Injections

To Compound 40 (50 g) and 400 g of glucose was added distilled water for injection with stirring until the total volume became 10 liters. The mixture was filtered for sterilization and placed into 2-ml colorless ampoules, and nitrogen gas was aerated therein followed by sealing, thereby producing injection preparations each having a volume of 10 ml per ampoule.

EXAMPLES

Given below are Examples of the present invention.

Example 1

Preparation of
5'-O-tert-butyldimethylsilyl-5-fluorouridine
(Compound 1)

A 1.50 g quantity of 5-fluorouridine (5.72 mmoles) was dissolved in 5 ml of N,N-dimethylformamide. To the solution were added 520 mg (7.64 mmoles) of imidazole and 633 mg (4.20 mmoles) of tert-butyldimethylsilyl chloride, and the reaction was conducted at room temperature for 15 hours. -The reaction mixture was ice-cooled, and 40 ml of water was added thereto. The reaction mixture was extracted three times with 40 ml of ethyl acetate. The organic layers were combined, washed three times with 50 ml of water and washed three times with 50 ml of a saturated aqueous sodium chloride solution and dried over anhydrous magnesium sulfate. The solvent was evaporated off under reduced pressure, and the residue thus obtained was subjected to silica gel column chromatography (chloroform: methanol=20:1). The eluate was concentrated and the residue was recrystallized from ether, giving 1.3 g of the title compound as white crystals. Yield: 60%.

Example 2

(a) Preparation of
5'-O-trityl-2'-O-tert-butyldimethyl-silyl-5-fluorouridine
(Compound A),
5'-O-trityl-3'-O-tert-butyldimethylsilyl-5-fluorouridine
(Compound B) and 5'-O-trityl-2', 3'-bis
(O-tert-butyldimethylsilyl)-5-fluorouridine (Compound C).

A 5.0 g quantity (9.99 mmoles) of 5'-O-trityl-5-fluorouridine was dissolved in 70 ml of N,N-dimethylformamide. To the solution were added 1.35 g (19.8 mmoles) of imidazole and 1.78 g (11.8 mmoles) of tert-butyldimethylsilyl chloride, and the reaction was effected at room temperature for 12 hours. The reaction mixture was ice-cooled, and extracted with 150 ml of ethyl acetate after adding 30 ml of water. The extract was dried over anhydrous magnesium sulfate. The solvent was evaporated off under reduced pressure, and the residue was subjected to silica gel column chromatography (chloroform: methanol =100:1), giving 1.3 g (yield 17.8%) of Compound C having Rf value of 0.65 (chloroform: methanol=50:1), 0.90 g (yield 14.6%) of Compound B having Rf value of 0.50 (chloroform: methanol=50:1) and 0.75 g (yield 12.2%) of Compound A having Rf value of 0.40 (chloroform: methanol=50:1).

(b) Preparation of
2'-O-tert-butyldimethylsilyl-5-fluorouridine
(Compound 2),
3'-O-tert-butyldimethylsilyl-5-fluorouridine
(Compound 3) and 2', 3'-bis
(O-tert-butyldimethylsilyl)-5-fluorouridine (Compound 4).

To 1.2 g (1.64 mmoles) of 5'-O-trityl-2'-O-tertbutyldimethylsilyl-5-fluorouridine (Compound A) obtained above was added 5 ml of 80% aqueous solution of acetic acid, and the mixture was stirred at 80° C. for 1 hour. After the reaction, the reaction mixture was evaporated under reduced pressure and the residue was subjected to silica gel column chromatography (chloroform: methanol=20:1). The eluate was concentrated and the residue obtained was recrystallized from ether, giving 0.40 g of Compound 2 as white crystals. Yield: 64.9%.

Following the above procedure and using 0.80 g (1.09 mmoles) of 5'-O-trityl-3'-O-tert-butyldimethylsilyl-5-fluorouridine (Compound B), 0.35 g of Compound 3 was prepared as white crystals. Yield: 85.3%. Similarly, from 1.1 g (1.50 mmoles) of 5'-O-trityl-2', 3'-his (O-tertbutyldimethylsilyl)-5-fluorouridine (Compound C), 0.65 g of Compound 4 was prepared as white crystals. Yield: 88.3%.

Example 3

Preparation of 2', 3',
5'-tri(O-tert-butyldimethylsilyl)-5-fluorouridine
(Compound 5), 2',
5'-bis(O-tert-butyldimethylsilyl)-5-fluorouridine
(Compound 6) and 3',
5'-bis(O-tert-butyldimethylsilyl)-5-fluorouridine
(Compound 7)

A 2 g quantity of 5-fluorouridine (7.63 mmoles) was dissolved in 5 ml of N,N-dimethylformamide. To the solution were added 1.24 g (18.3 mmoles) of imidazole and 2.98 g (19.1 mmoles) of tert-butyldimethylsilyl chloride, and the mixture was stirred at room temperature for 10 hours. The reaction mixture was ice-cooled, and 60 ml of water was added thereto. The reaction mixture was extracted with 300 ml of ethyl acetate. The extract was washed three times with 50 ml of a saturated aqueous sodium chloride solution and dried over anhydrous magnesium sulfate. The solvent was evaporated off under reduced pressure, and the residue thus obtained was subjected to silica gel column chromatography (benzene: ether=17:1), giving 0.97 g (yield 21%) of Compound 5 having Rf value of 0.40 (benzene: ether=17:1), 0.99 g (yield 26.4%) of Compound 7 having Rf value of 0.30 (benzene: ether=17:1) and 0.1 g (yield 2.7%) of Compound 6 having Rf value of 0.12 (benzene: ether=17:1).

Similarly, Compounds 8 to 34 shown in the following table I were prepared.

Table I and Table II each show 6 values (ppm) of $^1$H-NMR (solvent DMSO, internal standard TMS) and melting points (° C.) of Compounds 1 to 34 as well as Compounds A to C which are the intermediates of the present invention. In the following description, the values of coupling constant J in $^1$H-NMR spectrum data is expressed in terms of Hz.

TABLE I

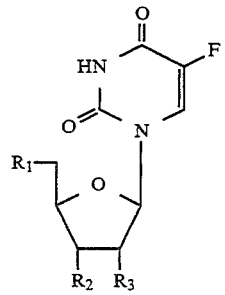

(I)

| Compound No. | Structure | | $^1$H-NMR δ (ppm) | Melting point (°C.) |
|---|---|---|---|---|
| 1 | $R_1$ | $-OSi(CH_3)_2-C(CH_3)_3$ | 0.90(9H, s)<br>0.10(6H, s)<br>3.66–4.08(5H, m)<br>5.06(1H, b)<br>5.49(1H, b)<br>5.73(1H, m)<br>8.01(1H, d, J=7.26)<br>11.85(1H, b) | 216–217 |
|  | $R_2$ | $-OH$ | | |
|  | $R_3$ | $-OH$ | | |
| 2 | $R_1$ | $-OH$ | 0.09(6H, s)<br>0.88(9H, s)<br>3.44–3.64(2H, m)<br>3.68–4.20(3H, m)<br>5.18–5.38(2H, b)<br>5.74(1H, m)<br>8.24(1H, d, J=7.2)<br>11.85(1H, b) | 91–92 |
|  | $R_2$ | $-OH$ | | |
|  | $R_3$ | $-OSi(CH_3)_2-C(CH_3)_3$ | | |
| 3 | $R_1$ | $-OH$ | 0.05(6H, s)<br>0.85(9H, s)<br>3.50–3.78(2H, m)<br>5.70(1H, m)<br>3.78–4.20(3H, m)<br>4.02(1H, d, J=21)<br>5.33(1H, t, J=15)<br>8.37(1H, d, J=7.5)<br>11.85(1H, b) | 75–77 |
|  | $R_2$ | $-OSi(CH_3)_2-C(CH_3)_3$ | | |
|  | $R_3$ | $-OH$ | | |
| 4 | $R_1$ | $-OH$ | 0.03(3H, s)<br>0.04(3H, s)<br>0.08(3H, s)<br>0.10(3H, s)<br>0.85(9H, s)<br>0.88(9H, s)<br>3.76(2H, m)<br>3.76–3.96(3H, m)<br>5.38(1H, b)<br>5.71(1H, m)<br>8.35(1H, d, J=7.5)<br>11.89(1H, b) | 177–177.5 |
|  | $R_2$ | $-OSi(CH_3)_2-C(CH_3)_3$ | | |
|  | $R_3$ | $-OSi(CH_3)_2-C(CH_3)_3$ | | |
| 5 | $R_1$ | $-OSi(CH_3)_2-C(CH_3)_3$ | 0.01(3H, s)<br>0.04(3H, s)<br>0.09(3H, s)<br>0.11(3H, s)<br>0.12(6H, s)<br>0.84(9H, s)<br>0.88(9H, s)<br>0.92(9H, s)<br>3.56–4.24(5H, m)<br>5.73(1H, m)<br>8.01(1H, d, J=7.0)<br>11.94(1H, b) | 77–78 |
|  | $R_2$ | $-OSi(CH_3)_2-C(CH_3)_3$ | | |
|  | $R_3$ | $-OSi(CH_3)_2-C(CH_3)_3$ | | |

TABLE I-continued (I)

[Structure: 5-fluorouracil attached to a deoxyribose-like sugar with substituents R1 (5'-position), R2 and R3 (on ring carbons)]

| Compound No. | Structure | $^1$H-NMR δ (ppm) | Melting point (°C.) |
|---|---|---|---|
| 6 | R1 —OSi(CH3)2—C(CH3)3<br>R2 —OH<br>R3 —OSi(CH3)2—C(CH3)3 | 0.09(12H, s)<br>0.84(9H, s)<br>0.88(9H, s)<br>3.50–4.20(5H, m)<br>5.41(1H, b)<br>5.75(1H, m)<br>7.98(1H, d, J=7.0)<br>11.87(1H, b) | Amorphous |
| 7 | R1 —OSi(CH3)2—C(CH3)3<br>R2 —OSi(CH3)2—C(CH3)3<br>R3 —OH | 0.04(6H)<br>0.11(6H, s)<br>0.84(9H, s)<br>0.90(9H, s)<br>3.68–4.12(5H, m)<br>5.09(1H, b)<br>5.73(1H, m)<br>8.02(1H, d, J=6.8)<br>11.89(1H, b) | 61–62 |
| 8 | R1 —OSi(CH3)2—(CH2)7CH3<br>R2 —OH<br>R3 —OH | 0.11(6H, s)<br>0.42–0.72(2H, m)<br>0.72–1.00(3H, m)<br>1.00–1.50(12H, b)<br>3.68–3.92(2H, m)<br>3.92–4.10(3H, m)<br>5.13(1H, b)<br>5.50(1H, b)<br>5.73(1H, m)<br>8.12(1H, d, J=7.3)<br>11.84(1H, b) | 120–121 |
| 9 | R1 —OH<br>R2 —OSi(CH3)2(CH2)7CH3<br>R3 —OH | 0.07(6H, s)<br>0.40–0.72(2H, m)<br>0.72–1.00(3H, m)<br>1.00–1.50(12H, b)<br>3.40–4.20(5H, m)<br>4.96(1H, b)<br>5.35(1H, b)<br>5.71(1H, m)<br>8.36(1H, d, J=7.48)<br>11.85(1H, b) | Amorphous |
| 10 | R1 —OH<br>R2 —OH<br>R3 —OSi(CH3)2(CH2)7CH3 | 0.10(6H, s)<br>0.40–0.72(2H, m)<br>0.72–1.00(3H, m)<br>1.00–1.50(12H, b)<br>3.40–4.20(5H, m)<br>5.22(1H, b)<br>5.38(1H, b)<br>5.74(1H, m)<br>8.25(1H, d, J=7.25)<br>11.85(1H, b) | Amorphous |

TABLE I-continued
(I)
| Compound No. | Structure | $^1$H-NMR δ (ppm) | Melting point (°C.) |
|---|---|---|---|
| 11 | 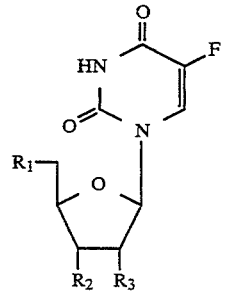
R$_2$ —OH
R$_3$ —OH | 0.67(3H, s)
3.52–4.18(5H, m)
5.17(1H, b)
5.44(1H, b)
5.73(1H, m)
7.14–7.72(10H, m)
7.97(1H, d, J=7.03)
11.86(1H, b) | 89–91 |
| 12 | 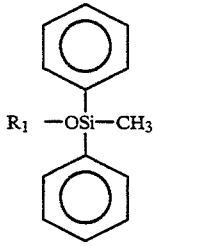
R$_2$ —OH
R$_3$ —OH | 3.68–4.16(5H, m)
5.18(1H, b)
5.46(1H, b)
5.74(1H, m)
7.18–7.64(15H, m)
7.91(1H, d, J=6.81)
11.86(1H, b) | 140–143 |
| 13 | 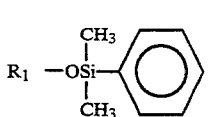
R$_2$ —OH
R$_3$ —OH | 0.40(6H, s)
3.62–4.12(5H, m)
5.11(1H, b)
5.48(1H, b)
5.72(1H, m)
7.28–7.44(3H, m)
7.44–7.62(2H, m)
8.10(1H, d, J=7.25)
11.85(1H, b) | 122–124 |
| 14 | 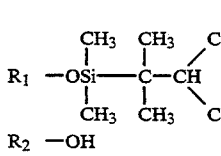
R$_2$ —OH
R$_3$ —OH | 0.13(6H, s)
0.84(6H, s)
0.86(6H, d, J=6.38)
1.61(1H, m)
3.64–4.08(5H, m)
5.09(1H, b)
5.50(1H, b)
5.72(1H, m)
7.96(1H, d, J=7.03)
11.87(1H, b) | 189–190 |

TABLE I-continued (I)

| Compound No. | Structure | $^1$H-NMR δ (ppm) | Melting point (°C.) |
|---|---|---|---|
| 15 | $R_1$ —OSi(C(CH$_3$)$_3$)(C$_6$H$_5$)$_2$<br>$R_2$ —OH<br>$R_3$ —OH | 1.02(9H, s)<br>3.66–4.08(5H, m)<br>5.16(1H, b)<br>5.51(1H, b)<br>5.78(1H, m)<br>7.24–7.50(6H, m)<br>7.50–7.70(4H, m)<br>8.01(1H, d, J=7.26)<br>11.85(1H, b) | 155–156 |
| 16 | $R_1$ —OSi(CH$_3$)$_2$CH$_2$C$_6$H$_5$<br>$R_2$ —OH<br>$R_3$ —OH | 0.08(6H, s)<br>2.23(2H, s)<br>3.64–4.08(5H, m)<br>5.10(1H, b)<br>5.48(1H, b)<br>5.70(1H, m)<br>6.80–7.28(5H, m)<br>8.04(1H, d, J=7.26)<br>11.89(1H, b) | 72–73 |
| 17 | $R_1$ —OH<br>$R_2$ —OSi(CH$_3$)$_2$CH$_2$C$_6$H$_5$<br>$R_3$ —OH | 0.11(6H, s)<br>2.25(2H, s)<br>3.48–5.32(5H, m)<br>5.04(1H, b)<br>5.34(1H, b)<br>5.78(1H, m)<br>6.84–7.40(5H, m)<br>8.41(1H, d, J=7.25)<br>11.90(1H, b) | Amorphous |
| 18 | $R_1$ —OH<br>$R_2$ —OH<br>$R_3$ —OSi(CH$_3$)$_2$CH$_2$C$_6$H$_5$ | 0.14(6H, s)<br>2.25(2H, s)<br>3.48–5.32(5H, m)<br>5.14(1H, b)<br>5.34(1H, b)<br>5.78(1H, m)<br>6.84–7.40(5H, m)<br>8.29(1H, d, J=7.47)<br>11.90(1H, b) | Amorphous |
| 19 | $R_1$ —OSi(C$_2$H$_5$)$_3$<br>$R_2$ —OH<br>$R_3$ —OH | 0.66(6H, t)<br>0.94(9H, q)<br>3.68–5.08(5H, m)<br>5.13(1H, b)<br>5.52(1H, b)<br>5.72(1H, m)<br>8.08(1H, d, J=7.25)<br>11.82(1H, b) | 153–154 |
| 20 | $R_1$ —OH<br>$R_2$ —OSi(C$_2$H$_5$)$_3$<br>$R_3$ —OH | 0.60(6H, t)<br>0.90(9H, q)<br>3.44–5.20(5H, m)<br>4.97(1H, b)<br>5.50(1H, b)<br>5.72(1H, m)<br>8.36(1H, d, J=7.26)<br>11.86(1H, b) | Amorphous |

TABLE I-continued

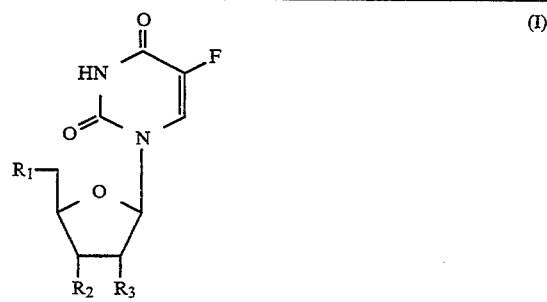
(I)

| Compound No. | Structure | | $^1$H-NMR δ (ppm) | Melting point (°C.) |
|---|---|---|---|---|
| 21 | $R_1$ | —OH | 0.60(6H, t) | Amorphous |
| | $R_2$ | —OH | 0.92(9H, q) | |
| | | $\quad\quad C_2H_5$ | 3.44–5.20(5H, m) | |
| | | $\quad\quad\|$ | 5.20(1H, b) | |
| | $R_3$ | $-OSi-C_2H_5$ | 5.33(1H, b) | |
| | | $\quad\quad\|$ | 5.72(1H, m) | |
| | | $\quad\quad C_2H_5$ | 8.24(1H, d, J=7.25) | |
| | | | 11.86(1H, b) | |
| 22 | | $\quad CH(CH_3)_2$ | 0.80–1.40(21H, b) | 163–165 |
| | | $\quad\quad\|$ | 3.70–4.10(5H, m) | |
| | $R_1$ | $-OSiCH(CH_3)_2$ | 5.09(1H, b) | |
| | | $\quad\quad\|$ | 5.50(1H, b) | |
| | | $\quad CH(CH_3)_2$ | 5.72(1H, m) | |
| | $R_2$ | —OH | 7.97(1H, d, J=7.1) | |
| | $R_3$ | —OH | 11.87(1H, b) | |
| 23 | $R_1$ | —OH | 0.80–1.20(21H, b) | Amorphous |
| | | $\quad CH(CH_3)_2$ | 3.48–4.38(5H, m) | |
| | | $\quad\quad\|$ | 5.10(1H, b) | |
| | $R_2$ | $-OSiCH(CH_3)_2$ | 5.35(1H, b) | |
| | | $\quad\quad\|$ | 5.72(1H, m) | |
| | | $\quad CH(CH_3)_2$ | 8.35(1H, d, J=7.48) | |
| | $R_3$ | —OH | 11.87(1H, b) | |
| 24 | $R_1$ | —OH | 0.80–1.20(21H, b) | Amorphous |
| | $R_2$ | —OH | 3.48–4.38(5H, m) | |
| | | $\quad CH(CH_3)_2$ | 5.22(1H, b) | |
| | | $\quad\quad\|$ | 5.38(1H, b) | |
| | $R_3$ | $-OSiCH(CH_3)_2$ | 5.74(1H, m) | |
| | | $\quad\quad\|$ | 8.16(1H, d, J=7.10) | |
| | | $\quad CH(CH_3)_2$ | 11.87(1H, b) | |
| 25 | | $\quad CH_3$ | 0.09(6H, s) | 186–188 |
| | | $\quad\quad\|$ | 0.94(7H, m) | |
| | $R_1$ | $-OSiCH(CH_3)_2$ | 3.64–4.08(5H, m) | |
| | | $\quad\quad\|$ | 5.12(1H, b) | |
| | | $\quad CH_3$ | 5.46(1H, b) | |
| | $R_2$ | —OH | 5.73(1H, m) | |
| | $R_3$ | —OH | 8.09(1H, d, J=7.03) | |
| | | | 11.84(1H, b) | |
| 26 | $R_1$ | —OH | 0.05(6H, s) | Amorphous |
| | | $\quad CH_3$ | 0.88(7H, m) | |
| | | $\quad\quad\|$ | 3.44–4.20(5H, m) | |
| | $R_2$ | $-OSiCH(CH_3)_2$ | 4.96(1H, b) | |
| | | $\quad\quad\|$ | 5.31(1H, b) | |
| | | $\quad CH_3$ | 5.72(1H, m) | |
| | $R_3$ | —OH | 8.37(1H, d, J=7.48) | |
| | | | 11.84(1H, b) | |
| 27 | $R_1$ | —OH | 0.08(6H, s) | Amorphous |
| | $R_2$ | —OH | 0.88(7H, m) | |
| | | $\quad CH_3$ | 3.44–4.20(5H, m) | |
| | | $\quad\quad\|$ | 5.31(1H, b) | |
| | $R_3$ | $-OSiCH(CH_3)_2$ | 5.44(1H, b) | |
| | | $\quad\quad\|$ | 5.72(1H, m) | |
| | | $\quad CH_3$ | 8.25(1H, d, J=7.25) | |
| | | | 11.84(1H, b) | |

TABLE I-continued

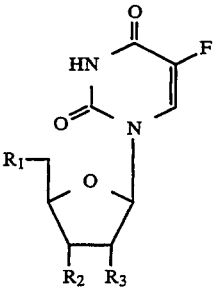

(I)

| Compound No. | Structure | | $^1$H-NMR δ (ppm) | Melting point (°C.) |
|---|---|---|---|---|
| 28 | $R_1$ | 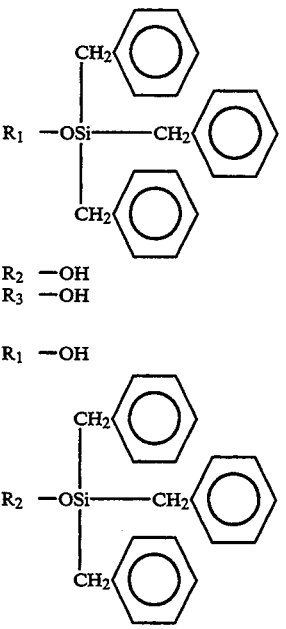 | 2.18(6H, s)<br>3.60–4.08(5H, m)<br>5.43(1H, b)<br>5.48(1H, b)<br>5.72(1H, m)<br>6.80–7.40(15H, m)<br>7.73(1H, d, J=6.82)<br>11.89(1H, b) | 85–86 |
| | $R_2$ —OH<br>$R_3$ —OH | | | |
| 29 | $R_1$ —OH<br>$R_2$ | 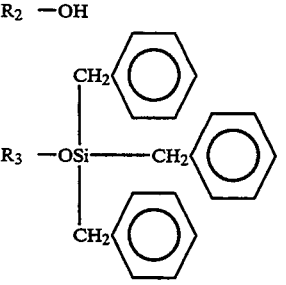 | 2.16(6H, s)<br>3.44–4.40(5H, m)<br>5.10(1H, b)<br>5.35(1H, b)<br>5.72(1H, m)<br>6.80–7.40(15H, m)<br>8.33(1H, d, J=7.48)<br>11.92(1H, b) | Amorphous |
| | $R_3$ —OH | | | |
| 30 | $R_1$ —OH<br>$R_2$ —OH<br>$R_3$ | (same silyl group as 29) | 2.15(6H, s)<br>3.44–4.40(5H, m)<br>5.35(1H, b)<br>5.60(1H, b)<br>5.72(1H, m)<br>6.80–7.40(15H, m)<br>8.22(1H, d, J=7.48)<br>11.90(1H, b) | Amorphous |
| 31 | $R_1$ | 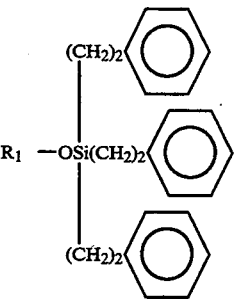 | 0.13(6H, s)<br>0.77–1.07(2H, m)<br>2.54–2.73(2H, m)<br>3.48–4.08(5H, m)<br>5.13(1H, b)<br>5.47(1H, b)<br>5.73(1H, m)<br>6.86–7.32(5H, m)<br>8.14(1H, d, J=7.25)<br>11.85(1H, b) | 60–62 |
| | $R_2$ —OH<br>$R_3$ —OH | | | |

TABLE I-continued

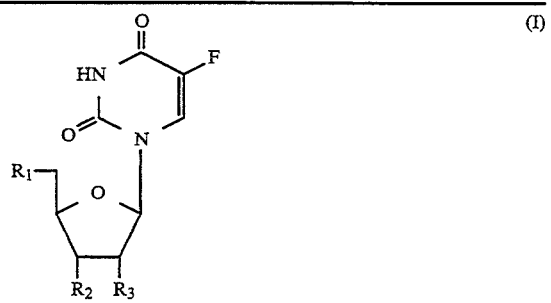
(I)

| Compound No. | Structure | | $^1$H-NMR δ (ppm) | Melting point (°C.) |
|---|---|---|---|---|
| 32 | $R_1$ | —OH | 0.10(6H, s) | Amorphous |
| | $R_2$ | —OSi(CH₃)₂(CH₂)₂—C₆H₅ | 0.78–1.06(2H, m) | |
| | | | 2.56–2.78(2H, m) | |
| | | | 3.48–4.22(5H, m) | |
| | | | 5.01(1H, b) | |
| | | | 5.33(1H, b) | |
| | $R_3$ | —OH | 5.78(1H, m) | |
| | | | 8.42(1H, d, J=7.47) | |
| | | | 11.91(1H, b) | |
| 33 | $R_1$ | —OH | 0.13(6H, s) | Amorphous |
| | $R_2$ | —OH | 0.78–1.06(2H, m) | |
| | | | 2.56–2.78(2H, m) | |
| | | | 3.48–4.22(5H, m) | |
| | $R_3$ | —OSi(CH₃)₂(CH₂)₂—C₆H₅ | 5.01(1H, b) | |
| | | | 5.33(1H, b) | |
| | | | 5.78(1H, m) | |
| | | | 8.28(1H, d, J=7.47) | |
| | | | 11.91(1H, b) | |
| 34 | $R_1$ | —OSi[CH(CH₃)₂]₂—O—SiOH[CH(CH₃)₂]₂ | 0.60–1.26(28H, m) | 165–166 |
| | | | 3.80–4.20(5H, m) | |
| | | | 5.11(1H, b) | |
| | | | 5.46(1H, b) | |
| | | | 5.77(1H, m) | |
| | | | 6.13(1H, b) | |
| | $R_2$ | —OH | 7.93(1H, d, J=7.03) | |
| | $R_3$ | —OH | 11.87(1H, b) | |

TABLE II

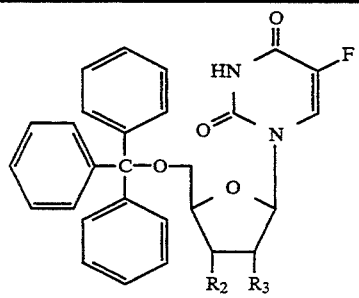
(II)

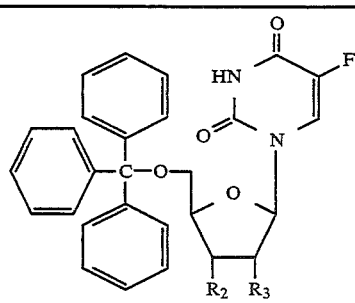
(II)

| Compound No. | Structure | | $^1$H-NMR δ (ppm) | Melting point (°C.) |
|---|---|---|---|---|
| A | $R_2$ | —OH | 0.06(6H, s) | Amorphous |
| | | | 0.80(9H, s) | |
| | | | 3.10–3.40(2H, m) | |
| | $R_3$ | —OSi(CH₃)₂—C(CH₃)₃ | 3.80–4.28(3H, m) | |
| | | | 5.35(1H, b) | |
| | | | 5.75(1H, m) | |
| | | | 7.38(15H, m) | |
| | | | 8.03(1H, d, J=7.30) | |
| | | | 11.92(1H, b) | |
| B | $R_2$ | —OSi(CH₃)₂—C(CH₃)₃ | 0.12(6H, s) | Amorphous |
| | | | 0.90(9H, s) | |
| | | | 3.04–3.60(2H, m) | |
| | | | 3.84–4.40(3H, m) | |
| | | | 5.20(1H, b) | |
| | $R_3$ | —OH | 5.75(1H, m) | |
| | | | 7.97(1H, d, J=6.8) | |
| | | | 7.39(15H, m) | |
| | | | 11.96(1H, b) | |

TABLE II-continued

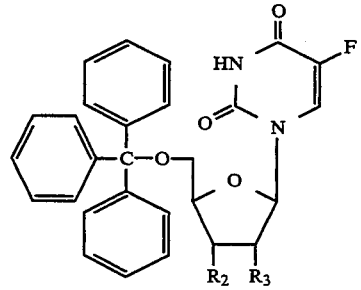

| Compound No. | Structure | $^1$H-NMR δ (ppm) | Melting point (°C.) |
|---|---|---|---|
| C | R$_2$ —OSi—C(CH$_3$)$_3$ with CH$_3$, CH$_3$ substituents; R$_3$ —OSi—C(CH$_3$)$_3$ with CH$_3$, CH$_3$ substituents | 0.06(3H, s) 0.08(3H, s) 0.12(6H, s) 0.81(9H, s) 0.91(9H, s) 3.00–3.42(2H, m) 3.92–4.42(3H, m) 5.76(1H, m) 7.41(15H, m) 8.05(1H, d, J=6.4) 11.99(1H, b) | Amorphous |

Example 4

Preparation of 5'-O-tert-butyldimethylsilyl-5-trifluoromethyl-2'-deoxyuridine (Compound 35)

A 1.0 g quantity of 5-trifluoromethyl-2'-deoxyuridine (3.6 mmoles) was dissolved in 3 ml of N,N-dimethylformamide. To the solution were added 0.49 g (7.2 mmoles) of imidazole and 0.64 g (4.3 mmoles) of tert-butyldimethylsilyl chloride, and the reaction was conducted at room temperature for 10 hours. The reaction mixture was treated in the same manner as in Example 1 with the exception of using chloroform/methanol (30:1) as an eluent for silica gel column chromatography, giving 0.6 g of the title compound as white crystals having a melting point of 199° to 200° C. Yield: 41%.

$^1$H-NMR (internal standard TMS, solvent d$_6$-DMSO, δ value, ppm)
11.9 (1H, b, N—3H)
8.1 (1H, s, 6—H)
6.03 (1H, t, J=6.8, 1—H)
5.28 (1H, b, —OH)
4.00 to 4.28 (1H, b, 3'—H)
3.84 to 4.00 (1H, m, 4'—H)
3.68 to 3.84 (2H, m, 5'—CH$_2$)
2.00 to 2.32 (2H, m, 2'—CH$_2$)
0.85 (9H, s, t-Bu)
0.05 (6H, s, —Si(CH$_3$)$_2$)

Example 5

Preparation of 3',5'-bis(O-tert-butyldimethylsilyl)-5-trifluoromethyl-2'-deoxyuridine (Compound 36)

A 1.0 g quantity of 5-trifluoromethyl-2'-deoxyuridine (3.6 mmoles) was dissolved in 5 ml of N,N-dimethylformamide. To the solution were added 1.02 g (15 mmoles) of imidazole and 1.14 g (7.60 mmoles) of tertbutyldimethylsilyl chloride, and the reaction was conducted at room temperature for 18 hours. The reaction mixture was treated in the same manner as in Example 4 to prepare 1.68 g of the title compound as white crystals having a melting point of 93° to 94° C.
Yield: 88.5%.

$^1$H-NMR (internal standard TMS, solvent d$_6$-DMSO, δ value, ppm)
11.9 (1H, b, N—3H)
8.1 (1H, s, 6—H)
6.03 (1H, t, J=6.1, 1'—H)
4.20 to 4.44 (1H, b, 3'—H)
3.80 to 4.00 (1H, b, 4'—H)
3.60 to 3.80 (2H, b, 5'—CH$_2$)
2.04 to 2.36 (2H, m, 2'—CH$_2$)
0.87, 0.86 (18H, s, t-Bu)
0.08, 0.05 (12H, s, —Si(CH$_3$)$_2$)

Example 6

Preparation of 5'-O-trityl-3'-O-tert-butyldimethylsilyl-5-trifluoromethyl-2'-deoxyuridine (Compound D) and 3'-O-tert-butyldimethylsilyl-5-trifluoromethyl-2'-deoxyuridine (Compound 37)

A 3.2 g quantity of 5'-O-trityl-5-trifluoromethyl-2'-deoxyuridine (5.9 mmoles) was dissolved in 5 ml of N,N-dimethylformamide. To the solution were added 0.82 g (12 mmoles) of imidazole and 1.26 g (8.3 mmoles) of tert-butyldimethylsilyl chloride, and the reaction was conducted at room temperature for 10 hours. The reaction product was purified in the same manner as in Example 4, giving 3.0 g of Compound D in an amorphous form. Yield: 94%.

$^1$H-NMR (internal standard TMS, solvent d$_6$-DMSO, δ value, ppm)
11.9 (1H, b, N—3H)
8.16 (1H, s, 6—H)
7.36 (15H, m, Ph)
6.07 (1H, t, J=7.0, 1'—H)
4.20 to 4.48 (1H, m, 3'—H)
3.80 to 4.04 (1H, m, 4'—H)
3.00 to 3.40 (2H, m, 5'—CH$_2$)
2.08 to 2.44 (2H, m, 2'—CH$_2$)
0.80 (9H, s, t-Bu) 0.03, −0.06 (6H, s, —Si(CH$_3$)$_2$)

A 5 ml of 80% aqueous solution of acetic acid was added to 2.9 g (5.38 mmoles) of the 5'-O-trityl-3'-O-tert-butyldimethylsilyl-5-trifluoromethyl-2'-deoxyuridine obtained above, and the mixture was stirred at 60° C. for 1 hour. After the reaction, the reaction mixture was extracted with a saturated aqueous sodium chloride solution-ethyl acetate and the extract was dried over anhydrous magnesium sulfate. Purification was conducted in the same manner as in Example 4, giving 0.32 g of Compound 37 in an amorphous form. Yield: 16%.

$^1$H-NMR (internal standard TMS, solvent d$_6$-DMSO, δ value, ppm)
11.8 (1H, b, N—3H)
8.67 (1H, s, 6—H)
6.05 (1H, t, J=6.1, 1'—H)
5.26 (1H, b, —OH)
4.24 to 4.52 ( 1H, b, 3'—H)
3.72 to 3.88 ( 1H, m, 4'—H)
3.40 to 3.72 (2H, m, 5'—CH$_2$)
2.00 to 2.40 (2H, m, 2'—CH$_2$)
0.87 (9H, s, t-Bu)
0.08 (6H, s, —Si(CH$_3$)$_2$)

Example 7

Compound 38 was prepared in the same manner as above.

5'-O-triisopropylsilyl-5-trifluoromethyl-2'-deoxyuridine (Compound 38)

Melting point 171° to 171.5° C.

$^1$H-NMR (internal standard TMS, solvent d$_6$-DMSO, δ value, ppm)

11.9 (1H, b, N—3H)
8.06 (1H, s, 6—H)
6.02 (1H, t, J=6.8, 1'—H)
5.32 (1H, d, J=4.4, —OH)
4.08 to 4.32 (1H, b, 3'—H)
3.64 to 4.00 (3H, m, 4'—H, 5'—CH$_2$)
2.08 to 2.32 (2H, m, 2'—CH$_2$)
0.60 to 1.32 (21H, m, —Si(iso-Pr)$_3$)

Example 8

Preparation of 5'-O-tert-butyldimethylsilyl-2', 3'-bis(O-dimethylglycyl)-5-fluorouridine (Compound 39)

To 60 ml of a solution containing 2.5 g (6.65 ml) of Compound 1 in methylene chloride were added 2.0 g (19.9 mmoles) of dimethylglycine, 5.3 g (43.9 mmoles) of N,N-dimethylaminopyridine and 6 g (20 mmoles) of 2-chloro-1-methylpyridinium tosylate. Thereafter the mixture was stirred at room temperature for 4 hours. After the reaction, the reaction mixture was extracted with ethyl acetate and water. The organic layer was washed with 0.1% cooled and diluted hydrochloric acid, and dried over magnesium sulfate. The organic layer was evaporated off, giving 3 g of Compound 39 in an amorphous form.

Yield: 82.6%

$^1$H-NMR (internal standard TMS, solvent d$_6$-DMSO, δ value, ppm)

0.12 (6H, s)
0.90 (9H, s)
2.21 (6H, s)
2.26 (6H, s)
3.17 to 3.41 (4H, m)
3.87 (2H, m)
4.24 (1H, m)
5.37 (2H, m)
5.99 (1H, m)
7.98 (1H, d, J=6.8)
11.96 (1H, br)

Example 9

Preparation of 5'-O-tert-butyldimethylsilyl-2', 3'-bis(O-dimethylglycyl)-5-fluorouridine malate (Compound 40) and tosylate (Compound 41)

To 20 ml of a solution containing 560 mg (1.0 mmole) of Compound 39 in ether was added 10 ml of a solution containing 287 mg (2.14 mmoles) of L-malic acid in ether, and the mixture was stirred at room temperature for 1 hour. The crystals precipitated were filtered, giving 800 mg of Compound 40 (yield: 98%). Similarly, 10 ml of a solution containing 96 mg (0.7 mmole) of p-toluenesulfonic acid in ether was added to 10 ml of a solution containing 200 mg (0.36 mmole) of Compound 39 in ether. Thereafter the mixture was stirred with ice-cooling for 30 minutes. The crystals precipitated were filtered, giving 245 mg of Compound 41. Yield: 95%. Compound 40 Melting point 95° to 97° C.

$^1$H-NMR (internal standard TMS, solvent d$_6$-DMSO, δ value, ppm)

0.12 (6H, s)
0.90 (9H, s)
2.26 (6H, s)
2.32 (6H, s)
2.40 to 2.60 (4H, m)
3.20 to 3.52 (4H, m)
3.88 (2H, m)
4.08 to 4.32 (3H, m)
5.41 (2H, m)
6.00 (1H, m)
6.00 to 7.60 (6H, br)
7.98 (1H, d, J=6.9)
11.90 (1H, br)

Compound 41
Amorphous $^1$H-NMR (internal standard TMS, solvent d$_6$-DMSO, value, ppm)

0.18 (6H, s)
0.96 (9H, s)
2.33 (6H, s)
2.88 (6H, s)
2.93 (6H, s)
3.90 to 4.41 (7H, m)
5.51 (2H, m)
6.19 (1H, m)
7.11 to 7.21 (4H, m)
7.50 to 7.58 (4H, m)
7.99 (1H, d, J=6.6)
10.04 (2H, br)
12.07 (1H, br)

Example 10

Preparation of 5'-O-(2,3-dimethyl-2-butyl)dimethylsilyl,-2',3'-bis(O-dimethylglycyl)-5-fluorouridine (Compound 42)

To 20 ml of a solution containing 1 g (2.47 mmoles) of Compound 14 in methylene chloride were added 763 mg (7.41 mmoles) of dimethylglycine, 1.99 g (16.32 mmoles) of N,N-dimethylaminopyridine and 2.23 g (7.43 mmoles) of 2-chloro-1-methylpyridinium tosylate. Thereafter the mixture was stirred at room temperature for 2 hours. After the reaction, the reaction mixture was extracted with ethyl acetate and water. The organic layer was washed with 0.1% cooled and diluted hydrochloric acid, and dried over magnesium sulfate. The organic layer was evaporated off, giving 1.24 g of Compound 42 in an amorphous form. Yield: 88%

$^1$H-NMR (internal standard TMS, solvent d$_6$-DMSO, δ value, ppm)

Compound 42
Amorphous 0.15 (6H, s)
0.85 (6H, s)
0.86 (6H, d, J=6.4)
1.40 to 1.80 (1H, m)
2.21 (6H, s)
2.26 (6H, s)
3.08 to 3.72 (4H, m)
3.86 (2H, m)
4.21 (1H, m)
5.36 (2H, m)
5.99 (1H, m)
7.94 (1H, d, J=6.6)
11.98 (1H, br)

Example 11

Preparation of 5'-O-(2,3-dimethyl-2-butyl)dimethylsilyl-2',3'-bis(O-dimethylglycyl)-5-fluorouridine malate (Compound 43)

To 20 ml of a solution containing 0.5 g (0.87 mmoles) of Compound 42 in ether was added 5 ml of a solution containing 233 mg (1.74 mmoles) of L-malic acid in ether, and the mixture was stirred at room temperature for 1 hour. The crystals precipitated were filtered, giving 687 mg of Compound 43. Yield: 93.7%.

Compound 43
Amorphous
$^1$H-NMR (internal standard TMS, solvent $d_6$-DMSO, δ value, ppm)
0.15 (6H, s)
0.85 (6H, s)
0.86 (6H, s)
1.40 to 1.80 (1H, m)
2.25 (6H, s)
2.31 (6H, s)
2.40 to 2.60 (4H, m)
3.20 to 3.72 (4H, m)
3.87 (2H, m)
4.04 to 4.32 (3H, m)
5.36 (2H, m)
5.98 (1H, m)
5.60 to 7.40 (7H, br)
7.96 (1H, d, J=6.8)

Example 12

Preparation of 5'-O-tert-butyldimethylsilyl-2',3'-bis(O-2-carboxyethylcarbonyl)-5-fluorouridine (Compound 44)

To 40 ml of a solution containing 2.0 g (5.44 mmoles) of Compound 1 in methylene chloride were added 2.18 g (21.76 mmoles) of succinic anhydride and 5.32 g (43.5 mmoles) of N,N-dimethylaminopyridine, and the mixture was stirred at room temperature for 8 hours. After the reaction, the reaction mixture was subjected to extraction after addition of 10% aqueous solution of citric acid and 500 mz of ether. The organic layer was washed with water and dried over magnesium sulfate. After evaporating the organic layer, the residue was recrystallized from n-pentane, giving 2.5 g of Compound 44 having a hygroscopic property.

Yield: 76.6%.
Compound 44
$^1$H-NMR (internal standard TMS, solvent $d_6$-DMSO, δ value, ppm)
0.11 (6H, s)
0.90 (9H, s)
3.33 to 3.49 (8H, m)
3.86 (2H, m)
4.18 (1H, m)
5.28 to 5.32 (2H, m)
6.02 (1H, m)
7.97 (1H, d, J=6.8)
12.00 to 12.23 (3H, br)

Example 13

Preparation of 5'-O-tert-butyldimethylsilyl-2',3'-bis(O-2-carboxyethylcarbonyl)-5-fluorouridine dipotassium salt (Compound 45)

To 100 ml of a solution containing 2.4 g (4.17 mmoles) of Compound 44 in ethyl acetate was added 3.2 g (17.38 mmoles) of potassium 2-ethylhexanoate, and stirred at room temperature for 14 hours. The crystals precipitated were filtered and purified with MCI gel (50 g, $H_2O \rightarrow H_2O$: $CH_3CN = 1:1$, product of Mitsubishi Chemical Industries Limited, Japan). The eluted fraction was lyophilized, giving 560 mg of Compound 45. Yield: 20.6%.

Compound 45
Melting point 195° to 197° C.
$^1$H-NMR (internal standard TMS, solvent $D_2O$, δ value, ppm)
0.18 (6H, s)
0.94 (9H, s)
2.41 to 2.70 (8H, m)
3.98 (2H, m)
4.40 (1H, m)
5.43 (2H, m)
6.17 (1H, m)
7.95 (1H, d, J=5.9)

Example 14

Preparation of 5'-O-tert-butyldimethylsilyl-3'-O-dimethylglycyl-5-trifluoromethyl-2'-deoxyuridine (Compound 46) and 5'-O-tert-butyldimethylsilyl-3'-O-dimethylglycyl-5-trifluoromethyl-2'-deoxyuridine malate (Compound 47)

Compounds 46 and 47 were prepared in the same manner as in Examples 10 and 11.

Compound 46
Amorphous
$^1$H-NMR (internal standard TMS, solvent $d_6$-DMSO, δ value, ppm)
0.10 (6H, s)
0.89 (9H, s)
2.00 to 2.60 (2H, m)
2.29 (6H, s)
3.00 to 3.76 (3H, m)
3.76 to 4.00 (2H, m)
4.20 (1H, m)
5.21 (1H, m)
6.07 (1H, t, J=2.9)
8.17 (1H, s)

Compound 47
Amorphous
$^1$H-NMR (internal standard TMS, solvent $D_2O$, δ value, ppm)
0.06 (6H, s)
0.86 (9H, s)
2.20 to 2.60 (4H, m)
2.34 (6H, s)
3.37 (2H, s)
3.68 to 3.88 (2H, m)
4.00 to 4.28 (2H, m)
4.32 to 5.08 (4H, b)
5.21 (1H, m)
6.11 (1H, t, J=3.7)
8.14 (1H, d, J=0.9)

Example 15

Preparation of 2', 3', 5'-tri(O-tert-butyldimethylsilyl)-5-trifluoromethyluridine (Compound 48)

To 6 ml of a solution containing 596 mg (2.1 mmoles) of 5-trifluoromethyluridine in N,N-dimethylformamide were added 1.14 g (16.7 mmoles) of imidazole and then 1.27 g (8.4 mmoles) of tert-butyldimethylchlorosilane, and the mixture was stirred at room temperature for 17 hours. After the reaction, the reaction mixture was subjected to extraction after addition of 30 ml of water and ethyl acetate (30 ml×3). The extract was washed with water (20 ml×3) and a saturated aqueous solution of sodium chloride (20 ml×1), and dried over anhydrous magnesium sulfate. The solvent was evaporated off under reduced pressure, and the residue thus obtained was subjected to silica gel column chromatography by elution with 3% methanol/chloroform, giving 1.28 g of Compound 48. Yield: 93%.

Compound 48

Amorphous $^1$H-NMR (internal standard TMS, solvent CDCl$_3$, δ value, ppm)

0.05, 0.09, 0.13, 0.16, 0.17 (18H, each s)
0.93, 0.97, 1.00 (27H, each s)
3.73 to 3.93 (2H, m)
4.08 to 4.23 (3H, m)
6.12 (1H, d, J=5.7)
8.20 (1H, d, J=1.1)
8.83 (1H, br)

Example 16

Preparation of 2′, 3′, 5′-tri(O-tert-butyldimethylsilyl)-5-fluorouridine (Compound 49)

Compound 49 was prepared in the same manner as in Example 15.

Compound 49

Amorphous $^1$H-NMR (internal standard TMS, solvent CDCl$_3$, δ value, ppm)

0.04, 0.05 (12H, each s)
0.88, 0.89 (18H, each s)
2.33 (3H, s)
2.89 (6H, s)
3.30 to 3.64 (2H, m)
4.05 to 4.38 (5H, m)
5.76 (1H, m)
7.16 (2H, m)
7.57 (2H, m)
8.02 (1H, d, J=7.04)
10.02 (1H, br)
11.94 (1H, m)

Pharmacological Test

Cells of mouse-transplantable tumor Sarcoma 180 (5×10$^6$ cells) were subcutaneously transplanted in the back of male mice of ICR/JCL strain (weighing 27 to 30 g). A solution or suspension of a test compound in a physiological saline solution containing 0.1% Tween 80 was administered intraperitoneally to mice (7 mice in each group) at a dose of 0.1 ml/10 g mouse body weight three times, namely on the 1st, 5th and 9th days, after the day of the transplantation.

A physiological saline solution of the same type but free of the test comopund was given in the same way as above to a control group.

On the 12th day after the transplantation, the tumor was weighed to calculate the average weight of the tumors for each dose in the group to which the test compound was given, and the weight was compared with the corresponding weight in the control group to determine the tumor growth inhibition ratio for each dose.

Table III below shows the results.

TABLE III

| Compound | Dose (mg/kg/day) | Tumor growth inhibition ratio (%) | Number of death (per 7 animals) |
|---|---|---|---|
| FUR | 20 | 16 | 0 |
|  | 35 | 54 | 0 |
|  | 50 | — | 7 |
| F$_3$TdR | 20 | 16 | 0 |
|  | 40 | 36 | 0 |
|  | 80 | 52 | 0 |
|  | 160 | 65 | 5 |
| 1 | 50 | 44 | 0 |
|  | 70 | 55 | 0 |
|  | 100 | 69 | 0 |
|  | 140 | 82 | 0 |
| 2 | 50 | 58 | 0 |
|  | 70 | 71 | 0 |
|  | 100 | 83 | 0 |
|  | 140 | 90 | 6 |
| 4 | 50 | 31 | 0 |
|  | 70 | 48 | 0 |
|  | 100 | 62 | 0 |
|  | 140 | 70 | 0 |
| 5 | 50 | 17 | 0 |
|  | 70 | 30 | 0 |
|  | 100 | 51 | 0 |
|  | 140 | 64 | 0 |
| 8 | 50 | 36 | 0 |
|  | 70 | 53 | 0 |
|  | 100 | 63 | 0 |
|  | 140 | 80 | 0 |
| 13 | 50 | 53 | 0 |
|  | 70 | 65 | 0 |
|  | 100 | 81 | 0 |
|  | 140 | 88 | 5 |
| 16 | 50 | 66 | 0 |
|  | 70 | 78 | 0 |
|  | 100 | 80 | 0 |
|  | 140 | 83 | 4 |
| 35 | 20 | 42 | 0 |
|  | 40 | 49 | 0 |
|  | 80 | 82 | 0 |
| 38 | 20 | 35 | 0 |
|  | 40 | 53 | 0 |
|  | 80 | 90 | 6 |
| 40 | 50 | 42 | 0 |
|  | 70 | 55 | 0 |
|  | 100 | 82 | 0 |
| 43 | 50 | 59 | 0 |
|  | 70 | 75 | 0 |
|  | 100 | — | 7 |
| 45 | 50 | 37 | 0 |
|  | 70 | 50 | 0 |
|  | 100 | 78 | 0 |

As seen from Table III, the compounds (I) of the invention have higher anti-tumor activity and lower toxicity compared with FUR and F$_3$TdR.

We claim:

1. A 5-substituted uridine compound of the formula

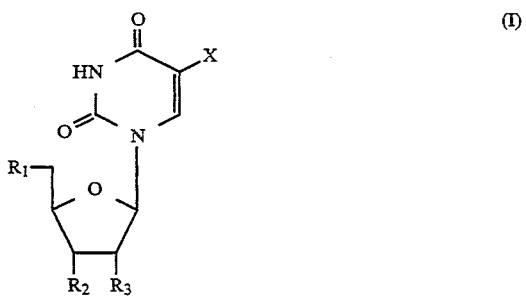

wherein

X is a fluorine atom, $R_1$, $R_2$ and $R_3$ each represents a member selected from the group consisting of a hydroxyl group and a group represented by the formula —OSi—($R_4$)($R_5$)($R_6$) provided that at least one of $R_1$, $R_2$ and $R_3$ is a group represented by the formula —OSi—($R_4$) ($R_5$) ($R_6$) wherein $R_4$ and $R_5$ are the same or different and each represents an alkyl group having 1 to 10 carbon atoms, and $R_6$ represents the group —OSi—($R_7$)($R_8$(OH) wherein $R_7$ and $R_8$ are the same or different and each represents a lower alkyl group having 1 to 6 carbon atoms; or a pharmaceutically acceptable salt thereof.

2. A composition containing a compound of claim 1 as an active ingredient in combination with a pharmaceutically acceptable vehicle.

3. A compound as defined in claim 1 wherein one of $R_1$, $R_2$ and $R_3$ is a group represented by the formula —OSi—($R_4$) ($R_5$)($R_6$) (wherein $R_4$, $R_5$ and $R_6$ are as defined above) and the remaining two of $R_1$, $R_2$ and $R_3$ represent hydroxyl group.

4. A compound as defined in claim 1 wherein $R_1$ is a group represented by the formula —OSi—($R_4$)($R_5$)($R_6$) (wherein $R_4$ and $R_5$ each represents an alkyl group having 1 to 10 carbon atoms and $R_6$ is a group represented by the formula —OSi—($R_7$)($R_8$)(OH) (wherein $R_7$ and $R_8$ are the same or different and each represents a lower alkyl group) and $R_2$ and $R_3$ each represents a hydroxyl group.

5. A compound as defined in claim 1 which is 5'—O—(tetraisopropyldisiloxane-1-yl-3-ol)-5-fluorouridine.

6. A 5-substituted uridine compound of the formula

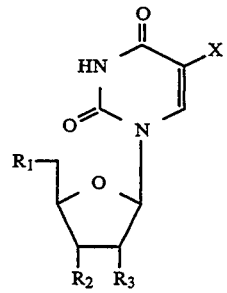

(I)

wherein

X is a fluorine atom, $R_1$, $R_2$ and $R_3$ each represents a member selected from the group consisting of a hydroxyl group, and a group represented by the formula —OSi—($R_4$)($R_5$)($R_6$) provided that at least one of $R_1$, $R_2$ and $R_3$ is a group represented by the formula —C-Si—($R_4$)($R_5$)($R_6$) wherein $R_4$, $R_5$ and $R_6$ are the same or different and $R_4$ and $R_5$ each represents a member selected from the group consisting of an alkyl group having 1 to 10 carbon atoms and a group represented by the formula —OSi—($R_7$) ($R_8$) (OH) wherein $R_7$ and $R_8$ are the same or different and each represents a lower alkyl group having 1 to 6 carbon atoms, and $R_6$ represents the group —OSi—($R_7$) ($R_8$) (OH); or a pharmaceutically acceptable salt thereof.

* * * * *